US012594154B2

(12) United States Patent
Jiao et al.

(10) Patent No.: US 12,594,154 B2
(45) Date of Patent: Apr. 7, 2026

(54) HYBRID BRAIDED STENT

(71) Applicant: SUZHOU ZENITH VASCULAR SCITECH LIMITED, SIP Suzhou (CN)

(72) Inventors: Liqun Jiao, SIP Suzhou (CN); Shuang Li, SIP Suzhou (CN); Jie Xia, SIP Suzhou (CN); Liyou Guo, SIP Suzhou (CN)

(73) Assignee: SUZHOU ZENITH VASCULAR SCITECH LIMITED, SIP Suzhou (CN)

( * ) Notice: Subject to any disclaimer, the term of this patent is extended or adjusted under 35 U.S.C. 154(b) by 854 days.

(21) Appl. No.: 17/914,228

(22) PCT Filed: Apr. 6, 2021

(86) PCT No.: PCT/CN2021/085635
§ 371 (c)(1),
(2) Date: Sep. 23, 2022

(87) PCT Pub. No.: WO2022/099986
PCT Pub. Date: May 19, 2022

(65) Prior Publication Data
US 2023/0346534 A1     Nov. 2, 2023

(30) Foreign Application Priority Data

Nov. 10, 2020    (CN) .......................... 202011249425.8

(51) Int. Cl.
*A61F 2/01*          (2006.01)

(52) U.S. Cl.
CPC ............ *A61F 2/013* (2013.01); *A61F 2/0105* (2020.05); *A61F 2220/0025* (2013.01); *A61F 2230/0067* (2013.01); *A61F 2230/0069* (2013.01)

(58) Field of Classification Search
CPC ...... A61F 2/88; A61F 2/90; A61F 2/07; A61F 2002/823; A61F 2/0105; A61F 2250/0017; A61F 2250/0028
See application file for complete search history.

(56) References Cited

U.S. PATENT DOCUMENTS

| | | | | | |
|---|---|---|---|---|---|
| 2004/0024416 A1* | 2/2004 | Yodfat | ...................... | A61F 2/90 | 623/1.53 |
| 2012/0168022 A1* | 7/2012 | Rasmussen | .......... | D03D 13/008 | 139/420 A |

(Continued)

FOREIGN PATENT DOCUMENTS

| | | |
|---|---|---|
| CN | 102764170 A | 11/2012 |
| CN | 202724037 U | 2/2013 |

(Continued)

OTHER PUBLICATIONS

First Office Action for Chinese Application No. 202011249425.8, dated Jul. 8, 2024, 8 pages.

(Continued)

*Primary Examiner* — Javier G Blanco
(74) *Attorney, Agent, or Firm* — Dickinson Wright PLLC

(57) ABSTRACT

A hybrid braided stent includes a stent body (20). The stent body (20) is a single-layer structure. The stent body (20) is a tubular structure formed by interweaving a plurality of filaments. The end areas of at least two of the plurality of filaments are different.

7 Claims, 9 Drawing Sheets

(56)                References Cited

U.S. PATENT DOCUMENTS

| 2012/0259407 | A1 |   | 10/2012 | Clerc et al. |   |
|---|---|---|---|---|---|
| 2012/0265294 | A1 |   | 10/2012 | Nishigishi |   |
| 2015/0148883 | A1 |   | 5/2015 | Hyodoh et al. |   |
| 2015/0282960 | A1 |   | 10/2015 | Harris |   |
| 2016/0199204 | A1 |   | 7/2016 | Pung et al. |   |
| 2016/0361180 | A1 |   | 12/2016 | Vong et al. |   |
| 2017/0304093 | A1 | * | 10/2017 | Düring | ..................... D04C 1/06 |
| 2018/0263797 | A1 | * | 9/2018 | Eller | ........................ A61F 2/90 |

FOREIGN PATENT DOCUMENTS

| CN |   | 105125326 | A |   | 12/2015 |   |
|---|---|---|---|---|---|---|
| CN |   | 105658174 | A |   | 6/2016 |   |
| CN |   | 106176002 | A |   | 12/2016 |   |
| CN |   | 107811728 | A |   | 3/2018 |   |
| CN |   | 108272487 | A |   | 7/2018 |   |
| CN |   | 110141409 | A |   | 8/2019 |   |
| CN |   | 110236734 | A |   | 9/2019 |   |
| CN |   | 111134920 | A |   | 5/2020 |   |
| CN |   | 111374810 | A |   | 7/2020 |   |
| CN |   | 111658251 | A |   | 9/2020 |   |
| CN |   | 112386364 | A |   | 2/2021 |   |
| CN |   | 214180706 | U |   | 9/2021 |   |
| EP |   | 3173052 | A1 |   | 5/2017 |   |
| WO |   | WO-2005011527 | A1 | * | 2/2005 | .............. A61F 2/90 |

OTHER PUBLICATIONS

English Translation of First Office Action for Chinese Application No. 202011249425.8, dated Jul. 8, 2024, 8 pages.
European Search Report for EP Application No. 21890521.4, dated Jan. 30, 2024, 10 pages.
International Search Report and Written Opinion for PCT Application No. PCT/CN2021/085635, dated Jul. 7, 2021, pp. 1-9.

* cited by examiner

22

21

22

20

24

25

HYBRID BRAIDED STENT

CROSS-REFERENCE TO RELATED APPLICATION(S)

This present application is a national stage application of International Patent Application No. PCT/CN2021/085635, filed Apr. 6, 2021, which claims priority to a Chinese Patent Application No. 202011249425.8 filed on Nov. 10, 2020, the disclosures of which are incorporated herein by reference in their entireties.

TECHNICAL FIELD

The application belongs to the technical field of medical devices, for example, relates to a hybrid braided stent.

BACKGROUND

Cerebrovascular disease is a major disease threatening human health and is the third leading cause of death following cardiovascular disease and tumor. 25% patients with ischemic stroke refer to carotid artery stenosis or occlusion.

Carotid artery stenosis is mainly treated by drug therapy, carotid endarterectomy and carotid artery stenting. With the advantages of simple operation, less trauma and less complications, carotid artery stenting is one of the effective methods for treating carotid artery stenosis. Carotid artery stents are generally mounted in the common carotid artery and the internal carotid artery. The carotid artery stent expands to enlarge the blood vessel narrowed by a lesion and restore normal blood supply in the blood vessel.

In the prior art, the common carotid artery stents mainly include cutting stents and braided stents.

Cutting stents are generally made of metal pipes having a tubular structure by laser cutting, mainly including stents having an open-loop structure and stents having closed-loop structure. The stent having an open-loop structure has a large mesh and cannot effectively cover the plaque. When the stent is released in the carotid artery stenosis site, the stent rod tends to cut the plaque and cause the plaque to break and fall off. The broken plaques falls off, enter the brain with the blood flow and then block the cerebral blood vessels, causing stroke and even death. The stent having a closed-loop structure has a small mesh, which can effectively cover the plaque. However, the stent provides too large supporting force and is difficult to pass through the tortuous lesions.

Braided stent is a kind of mesh stent formed by braiding metal wires (which are generally nickel titanium shape memory alloy wires). For example, there is a double-layer braided stent structure disclosed in the related art (US20160361180A1). The double-layer braided stent structure includes an outer braided stent and an inner metal mesh. The outer braided stent is formed by braiding thick metal wire, and provides the primary radial support force. However, the outer braided stent also has a large mesh and cannot prevent plaque from breaking and moving since it is difficult to cover the plaque. The inner metal mesh has a small mesh to effectively prevent plaque from flowing downstream in the blood vessel. The double-layer braided stent solves the problem that fragments flows downstream in the blood vessel when the plaque is broken. However, the outer braided stent and the inner metal mesh of the double-layer braided stent have different expansion rates, so it is difficult to accurately control the position accuracy of the outer braided stent and the inner metal mesh when the outer braided stent and the inner metal mesh are released to the predetermined position in the blood vessel. As a result, the inner metal mesh cannot be tightly pressed against the outer braided stent, resulting in the failure of the inner metal mesh to effectively prevent fragments from flowing downstream in the blood vessel.

In conclusion, the carotid artery stents in the related art has low safety.

SUMMARY

A hybrid braided stent is provided to solve the problem of low safety of carotid stents in the related art.

The following technical solutions are adopted in the application:

Provided is a hybrid braided stent including a stent body. The stent body is a single-layer structure. The stent body is a tubular structure formed by interweaving a plurality of filaments. The cross-sectional areas of at least two of the plurality of the filaments are different.

3

Figure 16:
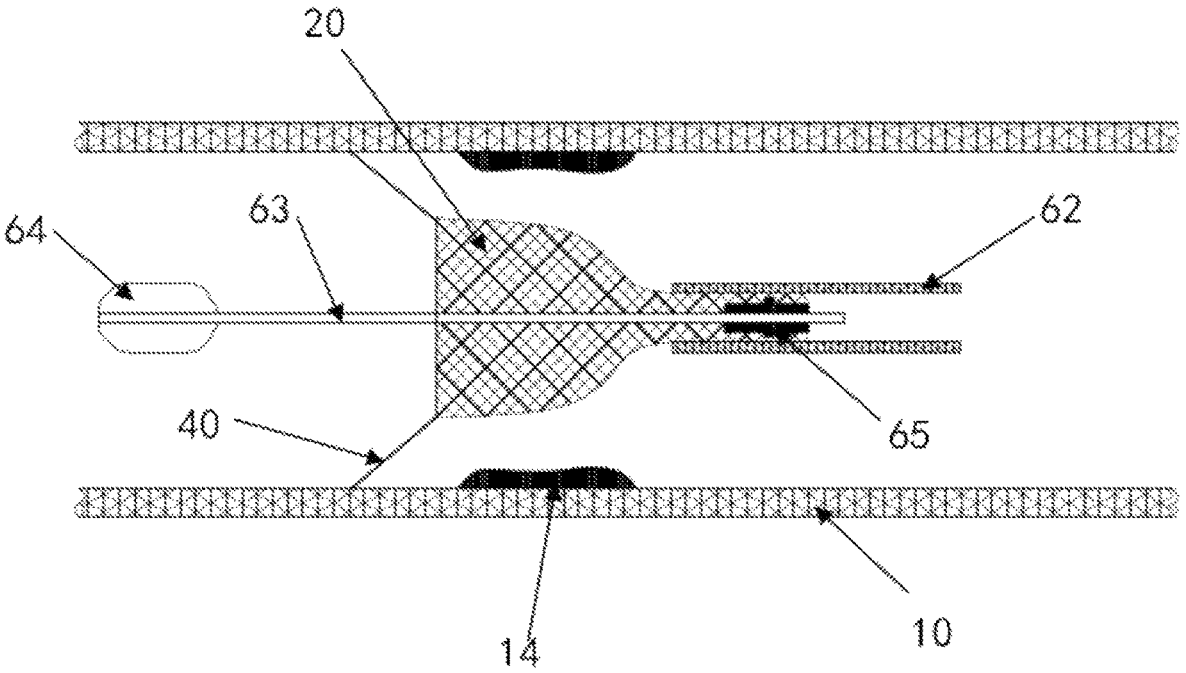
Figure 17:
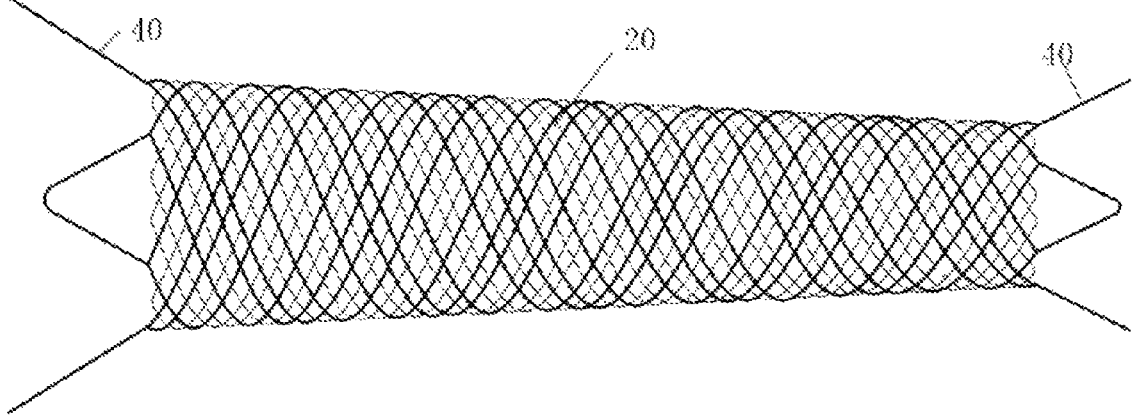
Figure 18:
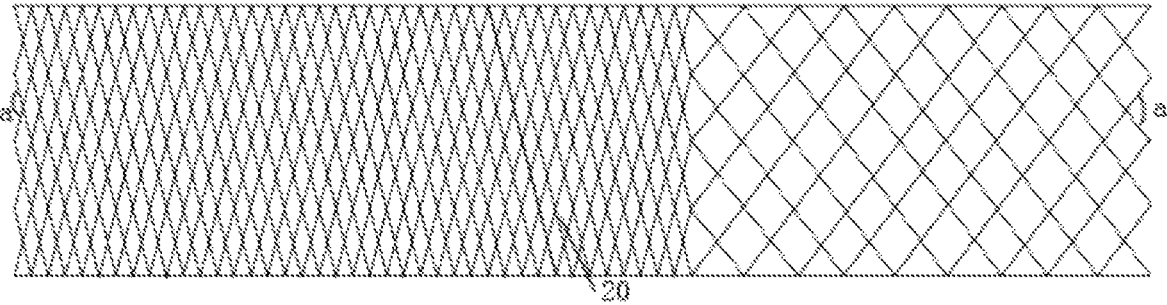

FIG. 16 is a process diagram illustrating a process when a hybrid braided stent is installed through a delivery assembly according to the embodiment of the application;

FIG. 17 is a diagram illustrating a structure of a third kind of stent body according to the embodiment of the application; and FIG. 18 is a structural sketch of a fourth kind of stent body according to the embodiment of the application.

REFERENCE LIST 10 carotid artery
11 common carotid artery
12 internal carotid artery
13 external carotid artery
14 plaque
20 stent body
21 fine filament
22 coarse filament
23 medium filament
24 proximal end
25 distal end
26 first bent portion
27 second bent portion
28 third bent portion
30 sleeve
40 dilator
41 stiffener
50 solder joint
60 delivery assembly
61 handle
62 guide tube
63 mandrel
64 head body
65 anchor
651 protrusion

DETAILED DESCRIPTION

Detailed description of the present application is made below in conjunction with the figures and the embodiments. It can be understood that the embodiments described herein are only used to explain the application. It should also be noted that for the purpose of description, the figures only show some parts related to the application, but not the structure in whole.

In description of the present application, unless otherwise expressly specified and limited, the terms "connected", "connect", and "fixed" should be interpreted broadly. For example, it may be a fixed connection, a detachable connection, or a connection into a whole; a mechanical connection or an electrical connection; a direct connection or indirect connection through an intermediate medium, an internal connection of two elements or the interaction between two elements. For those of ordinary skill in the art, the meanings of the above terms in the application can be understood depending on conditions.

In the application, unless otherwise expressly specified and limited, the case where the first feature is "on" or "under" the second feature may include the direct contact between the first and second features, and may also include other feature contact rather than direct contact between the first and second features. And the case where the first feature is "above", "over", and "on" the second feature indicates that the first feature is right and obliquely above the second feature, or only that the first feature is higher in level than the second feature. And the case where the first feature is "below", "under", and "underneath" the second feature indicates that the first feature is right and obliquely below the second feature, or only that the first feature is lower in level than the second feature. In description of the present embodiment, "up", "down", "right" and other terms describing orientations or positions are based on the orientations or positions shown in the figures. They are used only for convenient description and simplified operation, rather than indicating or implying that the device or element referred to must stay in a position, or be constructed and operated in an orientation. Besides, the terms "first" and "second" are used only for the purpose of distinguishing in description, with no special meaning.

Embodiment One

Figure 1:
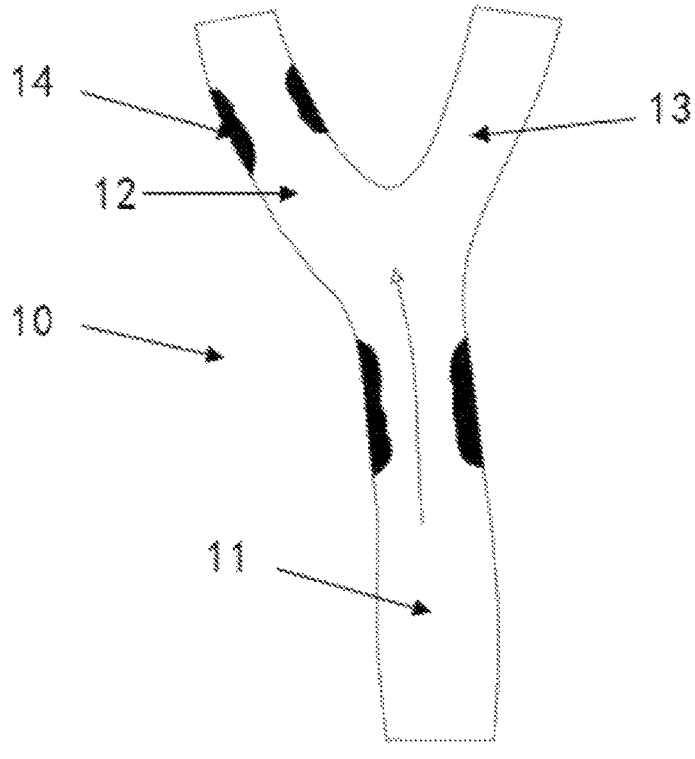
FIG. 1 is a schematic diagram illustrating a structure of the carotid artery according to the embodiment of the application.

FIG. 1 is a schematic diagram illustrating a structure of the carotid artery 10 according to the embodiment of the application. As shown in FIG. 1, carotid artery 10 includes a common carotid artery 11, an internal carotid artery 12 and an external carotid artery 13. The common carotid artery 11, the internal carotid artery 12 and the external carotid artery 13 form a Y-shaped bifurcation structure. The blood in the common carotid artery 11 flows into the internal carotid artery 12 and the external carotid artery 13 at the Y-shaped bifurcation structure. The blood in the internal carotid artery 12 mainly flows to the brain, while the blood in the external carotid artery 13 mainly supplies for facial organs. There are plaques 14 in the common carotid artery 11 and the internal carotid artery 12, which lead to vascular stenosis and block up blood flow. Therefore, it is necessary to implant a stent at the lesion to expand the blood vessels so that blood normally flows through the blood vessels.

Figure 2:
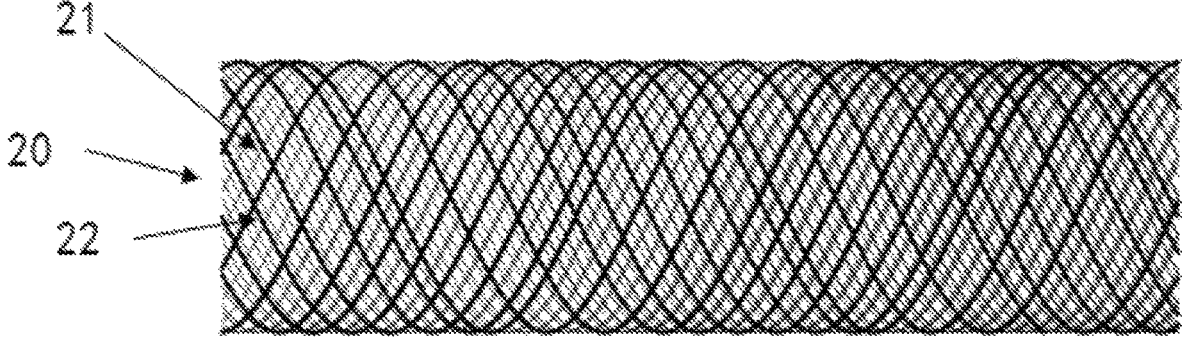
FIG. 2 is a diagram illustrating a local structure of a first kind of stent body according to the embodiment of the application.

FIG. 2 is a diagram illustrating a local structure of a first kind of stent body 20 according to the embodiment of the present disclosure. As shown in FIG. 2, this embodiment discloses a hybrid braided stent. The hybrid braided stent includes a stent body 20. The stent body 20 is a single-layer structure. The stent body 20 is a tubular structure formed by interweaving a plurality of filaments. For example, the stent body 20 can be cylindrical, or as shown in FIG. 17, the stent body 20 can be conical to adapt to the shape of the blood vessel. The cross-sectional areas of at least two of the filaments are different. When the stent body 20 is a conical structure, the diameter decreases gradually from the proximal end to the distal end. As the diameters of blood vessels are different in different positions, the conical structure can adapt to variations of diameters of the blood vessels. Compared with the cylindrical structure, the conical structure has a better fit with the blood vascular wall when implanted in the blood vessel, and the stent body 20 is less likely to cause excessive expansion of the blood vessel, and thus less likely damaging the blood vessel.

The hybrid braided stent in this embodiment is mainly applied to the stenosis of blood vessels. For example, it can be applied to the narrowed blood vessels at the Y-shaped bifurcation. The hybrid braided stent is mounted in the common carotid artery 11 and the internal carotid artery 12, so that the blood can enter the external carotid artery 13 through the mesh of the stent body 20, and ischemia is not caused in the external carotid artery 13.

Figure 5:
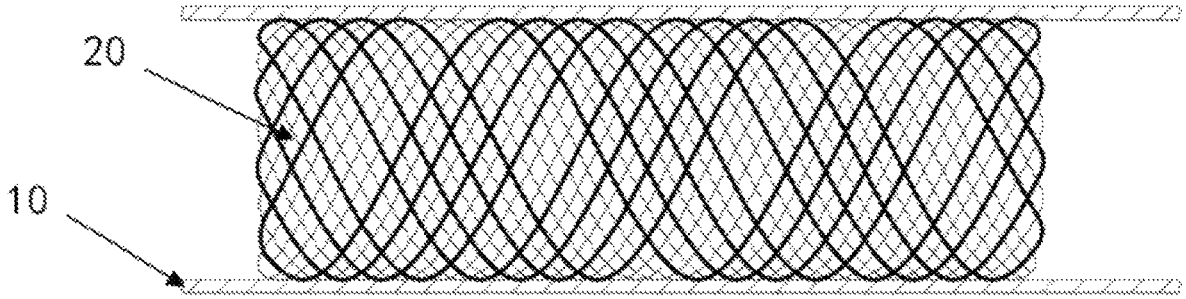
FIG. 5 is a diagram illustrating that the stent body matches with a blood vessel according to the embodiment of the application.

FIG. 5 is a diagram illustrating that the stent body 20 matches with a blood vessel according to the embodiment of the present disclosure. As shown in FIG. 5, in the present application, the stent body 20 of the hybrid braided stent is formed by interweaving at least two filaments, where at least two of the filaments have different cross-sectional areas. The filament with a large end area provides the stent body 20 with a sound supporting force, fit closely with the blood vessel and achieve good positioning. The filament with a small end area ensures that the meshes of the stent body 20 are small. When the stent body 20 is mounted in the blood vessel, the plaque 14 is stressed more uniformly and less likely to break. The stent body 20 can effectively prevent the plaque 14 fragments from flowing downstream in the blood vessel even if the plaque 14 is broken.

In conclusion, the stent body 20 of the application provides better safety during usage compared with the related art.

Moreover, each portion of the stent body 20 in this embodiment basically has the same expansion rate, and the stent body 20 can be compressed to a small volume, thus facilitating accurate positioning of the stent body 20 when the stent body 20 is mounted.

Figure 3:
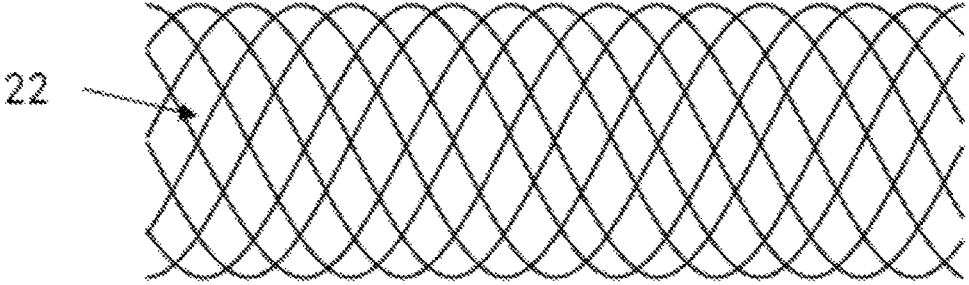
FIG. 3 is a diagram illustrating a structure of the main frame formed by braiding coarse filament according to the embodiment of the application.

As shown in FIG. 2, alternatively, the stent body 20 is formed by braiding two kinds of filaments with different cross-sectional areas. The materials of two kinds of filaments are different. In other embodiments, materials of the two kinds of filaments can be made of the same material. In an embodiment, the two kinds of filaments may be a fine filament 21 and a coarse filament 22 respectively. The end area of fine filament 21 is smaller than the end area of coarse filament 22. FIG. 3 is a diagram illustrating a structure of the main frame formed by braiding coarse filament 22 according to the embodiment of the present disclosure. As shown in FIG. 3, the main frame formed by braiding coarse filament 22 has a large mesh. For example, the mesh has a size ranging from 1 mm to 20 mm, alternatively, from 1 mm to 10 mm. The mesh referred to in this application can be circular, diamond or rectangle etc. For a non-circular mesh, the size refers to the diameter of inscribed circle of the mesh. The main frame is mainly used to provide the supporting force between blood vessels.

As shown in FIGS. 2 and 3, the fine filament 21 and the coarse filament 22 are mixed and braided together. The total number of fine filaments 21 and coarse filaments 22 is at least 18, where the number of coarse filaments 22 is at least 6 and the number of fine filaments 21 is at least 12. Fine filaments 21 and coarse filaments 22 are uniformly distributed. The braided stent body 20 can also be shaped by heat treatment, for example, heat treatment is performed at a temperature ranging from 400° C. to 600° C. for a time ranging from 30 s to 20 min. The weaving angle of fine filaments 21 and coarse filaments 22 may range from 90° to 180°.

Alternatively, the end face of the filament in this embodiment can be circular. At this time, diameter of the fine filament 21 ranges from 0.01 mm to 0.5 mm, alternatively from 0.01 mm to 0.2 mm. The diameter of the coarse filament 22 ranges from 0.05 mm to 1.0 mm, alternatively from 0.1 mm to 0.5 mm. In other embodiments, the end face of the filament can also be rectangular, that is, the filament is a flat structure.

Due to the existence of the fine filament 21, the stent body 20 has a smaller mesh and can prevent the fragments of plaque 14 from flowing downstream in the blood vessel. For example, the size of the mesh of the stent body 20 may ranges from 0.05 mm to 2 mm, alternatively from 0.1 mm to 1 mm.

Both fine filaments 21 and coarse filaments 22 are made of medical metal wire. Medical metal materials include medical stainless steel, nickel titanium shape memory alloy, cobalt base alloy, titanium alloy, magnesium alloy, or the like, alternatively nickel titanium shape memory alloy.

When the stent body 20 is released in the blood vessel, the stent body 20 can expand to fit with the blood vessel and enlarge the blood vessel, and be positioned at the mounting position. The stent body 20 has good flexibility and can adapt to blood vessels having different diameters and shapes.

Figure 4:
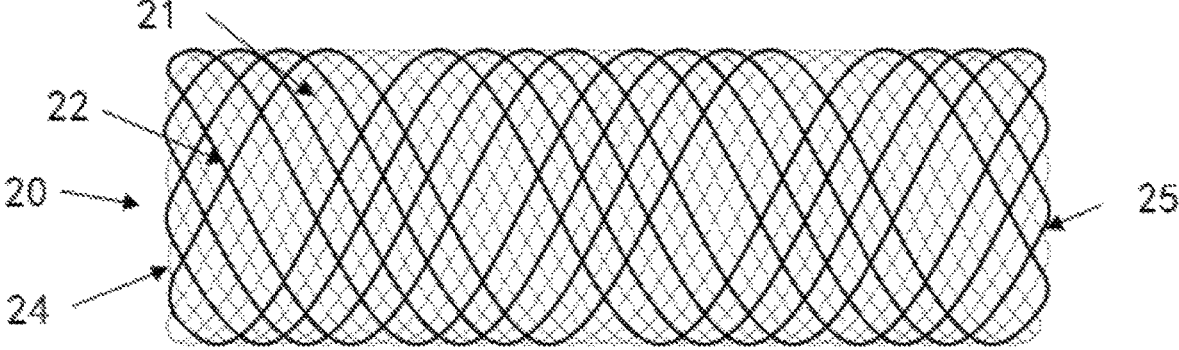
FIG. 4 is a diagram illustrating an overall structure of a first kind of stent body according to the embodiment of the application.

FIG. 4 is a diagram illustrating an overall structure of a first kind of stent body 20 according to the embodiment of the application. As shown in FIG. 4, alternatively, the ends of at least two filaments located at one or both ends of the stent body 20 are connected together such that the end of the filaments is closed. The ends of two filaments of the same kind can be connected together, or the ends of two filaments of different kinds can be connected together. The two ends of the stent body 20 are the proximal end 24 and the distal end 25 respectively. The distal end 25 can be considered as the end that enters the blood vessel firstly when mounting. The closure of end of the filaments at proximal end 24 and distal end 25 makes the proximal end 24 and the distal end 25 smoother and less likely to damage the blood vessel. Moreover, it can also improve the supporting force of the stent body 20 and the storage capacity of the stent body 20 during contraction of the stent body 20.

Figure 6:
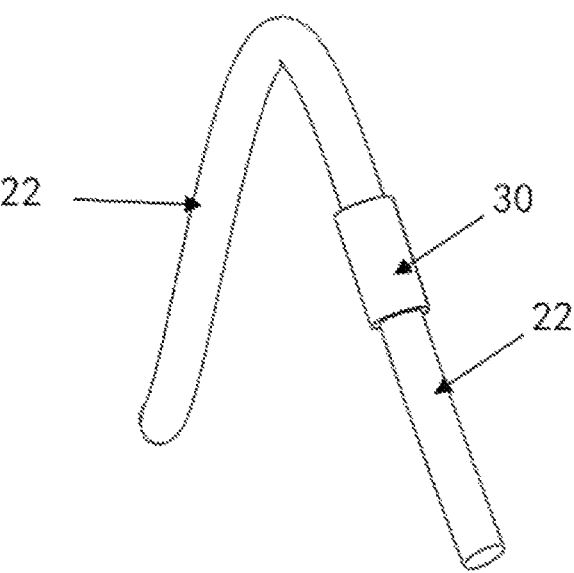
FIG. 6 is a diagram illustrating a first connection mode of ends of two filaments according to the embodiment of the application.
Figure 7:
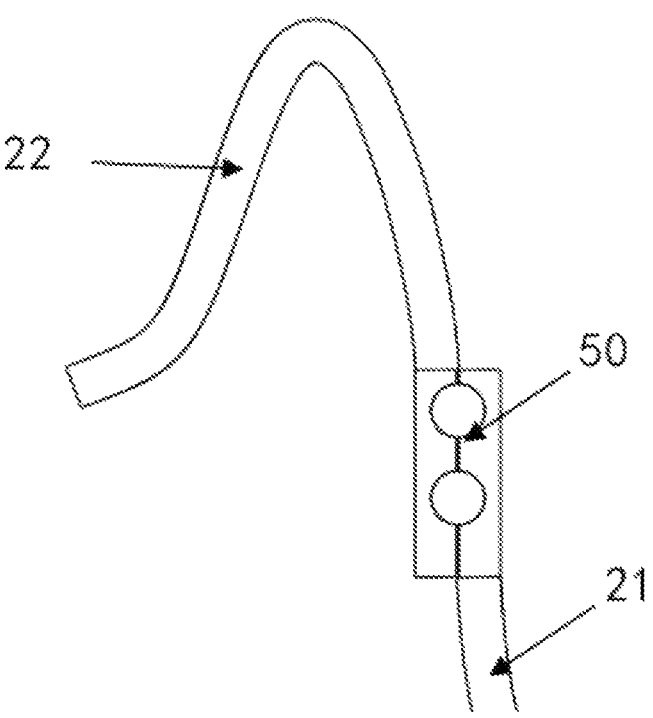
FIG. 7 is a diagram illustrating a second connection mode of ends of two filaments according to the embodiment of the application.

FIG. 6 is a diagram illustrating a first connection mode of ends of two filaments according to the embodiment of the application. FIG. 7 is a diagram illustrating a second connection mode of ends of two filaments according to the embodiment of the application. Alternatively, as shown in FIG. 6, the ends of each two filaments of the proximal end 24 and the distal end 25 are connected together through the sleeve 30. Alternatively, as shown in FIG. 7, the ends of each two filaments of the proximal end 24 and the distal end 25 are welded together by laser such that the ends of the two filaments are connected to form a closed curve. In other embodiments, the ends of each two filaments of the proximal end 24 and the distal end 25 can also be connected together by glue.

As shown in FIG. 6, the inner diameter of the sleeve 30 ranges from 0.01 mm to 0.1 mm larger than diameter of the two filaments. The wall thickness of the sleeve 30 ranges from 0.01 mm to 0.2 mm, and the length of the sleeve 30 ranges from 0.5 mm to 5 mm. The sleeve 30 can be made of nickel titanium alloy, medical stainless steel, cobalt base alloy, titanium alloy or magnesium alloy etc. Alternatively, the sleeve 30 can also be made of the developing materials such as platinum iridium alloy, gold, tantalum, platinum and platinum tungsten alloy, so that the sleeve 30 is radiopaque and is helpful to position the stent body 20. The connection process is as follows: sleeve the sleeve 30 on the ends of the two filaments, and then connect the sleeve 30 with the ends of the two filaments by glue, laser or welding such that the sharp ends of the filaments are eliminated.

As shown in FIG. 7, the welding process is as follows: arrange the ends of the two filaments side by side, and then create one or more solder joints 50 at the ends of the two filaments by laser to connect the ends of the two filaments together, so that the sharp ends of the filaments are eliminated.

In other embodiments, the ends of more than three filaments may also be connected together at the same time, to eliminate the sharp ends of the filaments. In a word, it is necessary to ensure that the stent body 20 is provided with no sharps after being weaved, so that the blood vessel is protected. The supporting force between the stent body 20 and the blood vessel should also be set on the condition that no damage to the blood vessel is caused.

Figure 12:
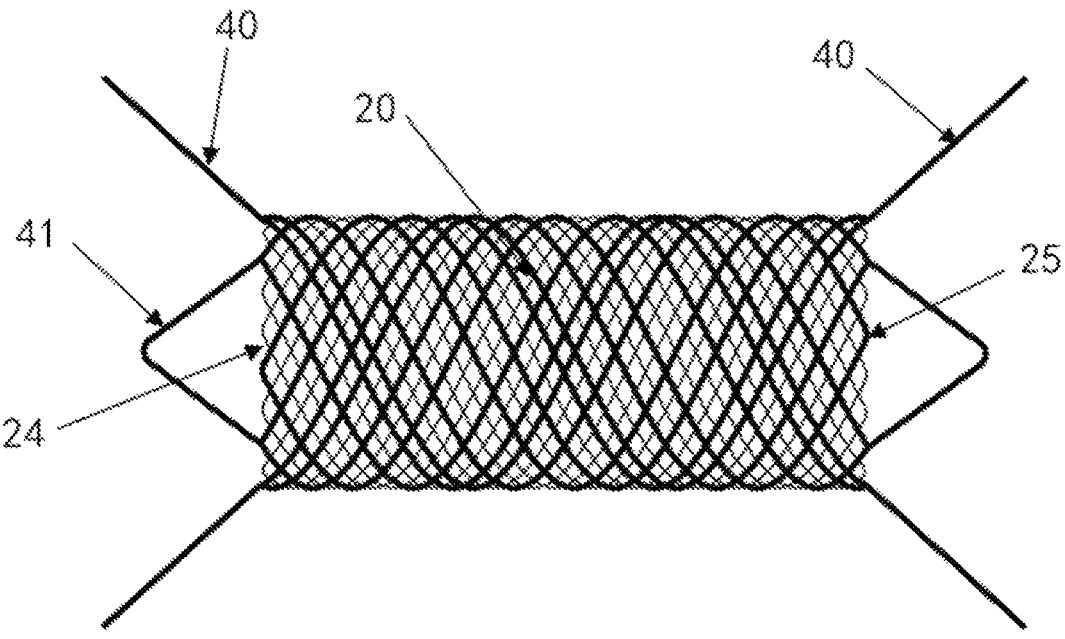
FIG. 12 is a diagram illustrating a connection between the stent body and the dilator according to the embodiment of the application.

FIG. 12 is a diagram illustrating a connection between the stent body 20 and the dilator 40 according to the embodiment of the application. As shown in FIG. 12, alternatively, the hybrid braided stent further includes a dilator 40. The dilator 40 is mounted at the end of the stent body 20, and the diameter of the dilator 40 is configured to gradually increase in the direction away from the stent body 20. The diameter of the dilator 40 is larger than the diameter of the stent body 20. When the hybrid braided stent is released in the blood vessel, there is a greater supporting force between the dilator 40 and the blood vessel, to improve the overall positioning effect of the hybrid braided stent. The dilator 40 further includes a stiffener 41. The stiffener 41 and one of the proximal end 24 or the distal end 25 constitutes a triangular structure. The stiffener 41 can improve the supporting force between the dilator 40 and the blood vessel, and can also store energy for the dilator 40 when the dilator 40 is retracted.

Alternatively, at least one of the filaments is radiopaque, so that it can further improve the developability of the hybrid braided stent, as well as the mounting accuracy and convenience of the hybrid braided stent. The radiopaque filament can be made of platinum-iridium alloy, gold, tantalum, platinum, and platinum tungsten alloy, etc.

Alternatively, the surface of the filament is provided with a smooth insulating layer, so that the friction between adjacent filaments is reduced. The smooth insulating layer can also increase smoothness of the stent body 20 in expansion and contraction. Besides, the smooth insulating layer ensures that the surface of the filament is smooth, reduces the friction between the stent body 20 and the guide tube 62, and reduces resistance of the stent body 20 when the stent body 20 is delivered, thus facilitating pushing and releasing of the stent body 20. And the smooth insulating layer can also prevent thrombosis. The smooth insulating layer can be made of parylene or be a coating made of derivative of the parylene.

As materials of the filaments are different, there is a potential difference generated between filaments of different materials, thus generating electrochemical corrosion, the generating electrochemical corrosion may lead to release of metal ions, decrease in supporting force of the stent body 20, and even breakage of the filaments. The smooth insulating layer provided in the embodiment can prevent metal ions on the filament from entering the blood, avoid electrochemical corrosion, and protect the filament.

Figure 11:
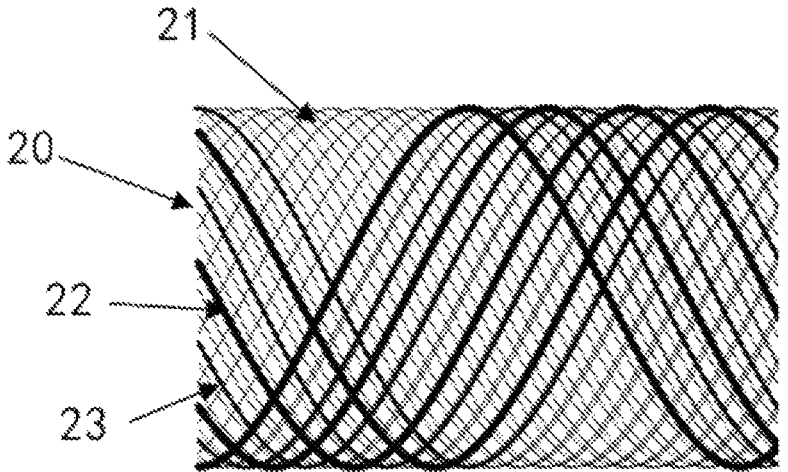
FIG. 11 is a diagram illustrating a structure of a second kind of stent body according to the embodiment of the application.

FIG. 11 is a diagram illustrating a structure of a second kind of stent body 20 according to the embodiment of the present disclosure. As shown in FIG. 11, alternatively, the stent body 20 is formed by braiding three kinds of filaments with different cross-sectional areas. The materials of the three filaments are not exactly the same. In other embodiments, the three filaments may be made of the same material. The three filaments with different cross-sectional areas are fine filament 21, coarse filament 22 and medium filament 23 respectively. The end area of the medium filament 23 is larger than the end area of the fine filament 21 and smaller than the end area of the coarse filament 22. The medium filament 23 plays a role of transition and regulation, so that the stent body 20 has a proper supporting force and mesh size. The supporting force and mesh size of the stent body 20 can be adjusted by changing the end area and material of the medium filament 23. The diameter of the medium filament 23 may range from 0.02 mm to 0.8 mm, alternatively from 0.05 mm to 0.3 mm.

Figure 8:
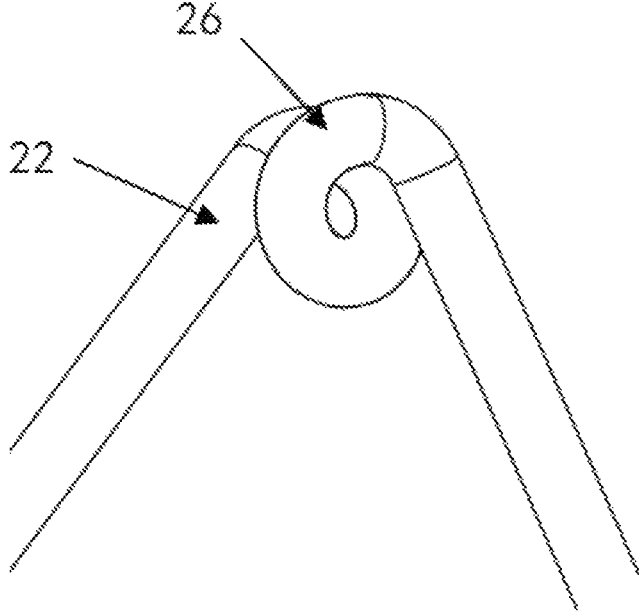
FIG. 8 is a diagram illustrating a structure of a first bent portion of a filament according to the embodiment of the application.
Figure 9:
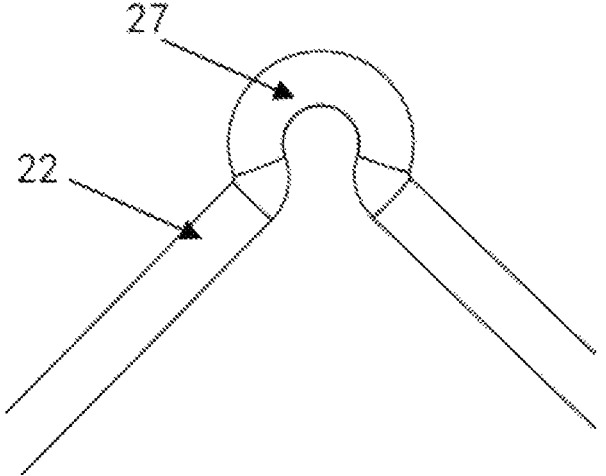
FIG. 9 is a diagram illustrating a structure of a second bent portion of a filament according to the embodiment of the application.
Figure 10:
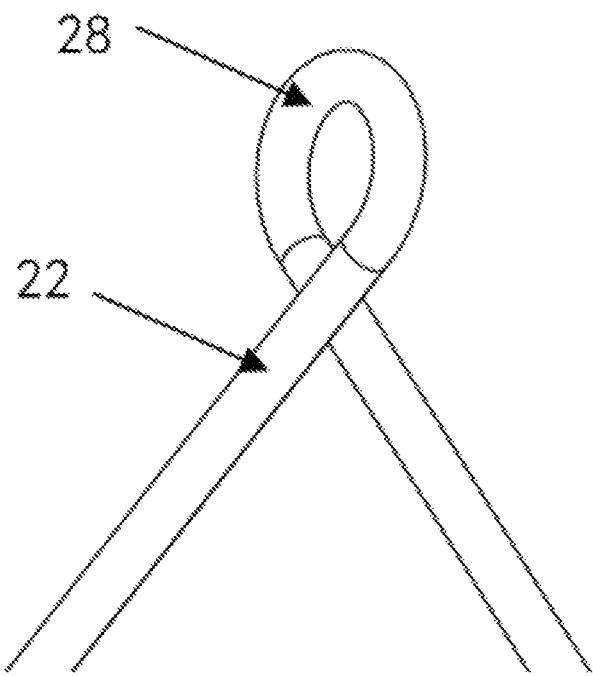
FIG. 10 is a diagram illustrating a structure of a third bent portion of a filament according to the embodiment of the application.

FIG. 8 is a diagram illustrating a structure of a first bent portion 26 of a filament according to the embodiment of the application. FIG. 9 is a diagram illustrating a structure of a second bent portion 27 of a filament according to the embodiment of the application. FIG. 10 is a diagram illustrating a structure of a third bent portion 28 of a filament according to the embodiment of the application. As shown in FIGS. 8 to 10, the first bent portion 26 is a spring-shaped structure, and the second bent portion 27 is an Ω-shaped structure. Since the Q-shaped structure is partially open, the Ω-shaped structure can store energy. The third bent portion 28 is a closed annular structure. The filament at the end of the stent body 20 is provided with a first bent portion 26, or a second bent portion 27, or a third bent portion 28. The first bent portion 26, the second bent portion 27 or the third bent portion 28 is provided with a socket configured to be inserted into by the protrusion 651 of the delivery assembly 60. For the second bent portion 27 with an opening, when the stent body 20 is located in the guide tube 62 of the delivery assembly 60, the second bent portion 27 is in a closed state, to be reliably inserted into by and matched with the protrusion 651, and less likely to be separated from the protrusion 651.

The first bent portion 26, or the second bent portion 27, or the third bent portion 28 is used to prevent the stent body 20 from plastic deformation when it enters into the guide tube 62 of the delivery assembly 60. The first bent portion 26, the second bent portion 27 and the third bent portion 28 can store energy. When the stent body 20 extends from the guide tube 62, the stent body 20 has a larger expansion force. The expansion force is set on the condition that no damage is caused to the blood vessel.

Figure 13:
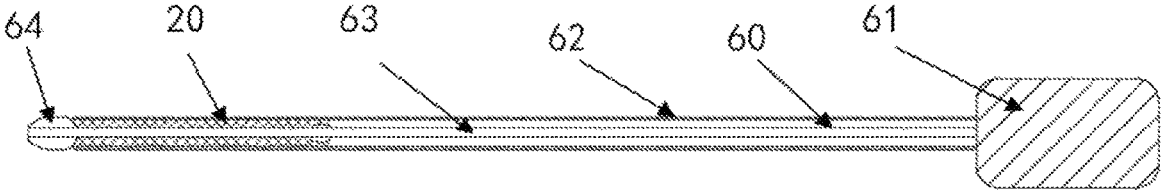
FIG. 13 is a diagram illustrating that a hybrid braided stent matches with a delivery assembly according to the embodiment of the application.
Figure 14:
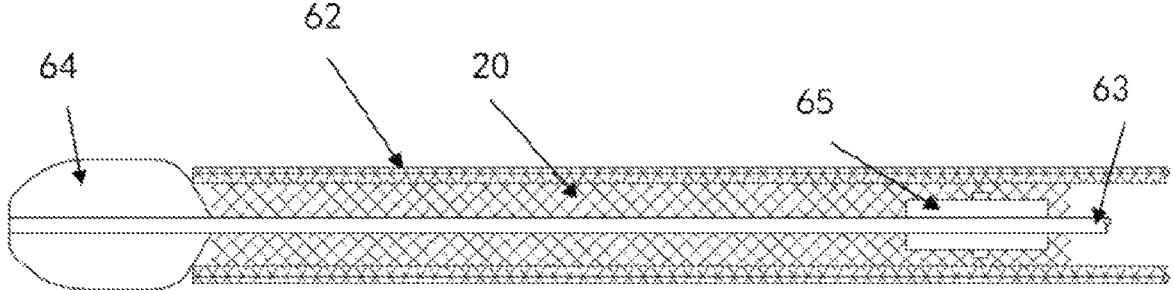
FIG. 14 is a local view illustrating that the hybrid braided stent matches with the delivery assembly according to the embodiment of the application.
Figure 15:
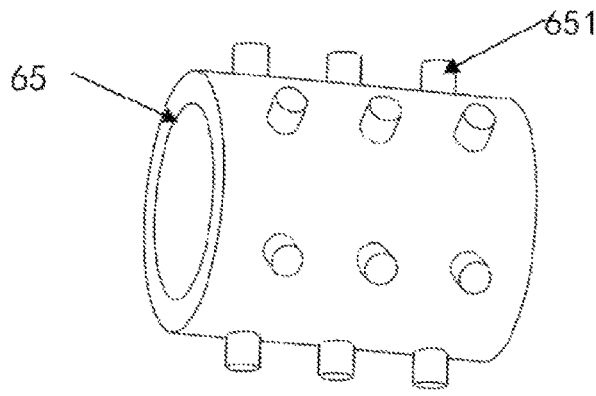
FIG. 15 is a stereogram illustrating an anchor according to the embodiment of the application.

FIG. 13 is a diagram illustrating that a hybrid braided stent matches with a delivery assembly 60 according to the embodiment of the application. FIG. 14 is a local view illustrating that the hybrid braided stent matches with the delivery assembly 60 according to the embodiment of the application. FIG. 15 is a stereogram illustrating an anchor 65 according to the embodiment of the application. FIG. 16 is a process diagram illustrating a process when a hybrid braided stent is installed through a delivery 60 assembly according to the embodiment of the application.

As shown in FIGS. 13 to 16, the delivery assembly 60 is used to deliver the hybrid braided stent to a predetermined position in the blood vessel and recover the hybrid braided stent. The delivery assembly 60 includes a handle 61, a guide tube 62, a mandrel 63, a head body 64, and an anchor 65. The handle 61 and the head body 64 are mounted at the front end and the rear end of the mandrel 63 respectively. The mandrel 63 is movably located in the guide tube 62. The anchor 65 is mounted in the middle and rear of the mandrel 63. The protrusion 651 on the anchor 65 is used to insert into and match with the first bent portion 26, the second bent portion 27 or the third bent portion 28 of the proximal end 24 of the stent body 20, making it convenient to release the stent body 20 out of the guide tube 62, and timely recover the hybrid braided stent into the guide tube 62 when the mounting position is found to be inaccurate.

The stent body 20 and the dilator 40 can be sleeved on the mandrel 63 and compressed into the guide tube 62. The handle 61 is pulled backward to release the hybrid braided stent. The dilator 40 at the distal end 25 is anchored with the blood vessel firstly to prevent movement of the hybrid braided stent during the releasing process. The handle 61 is pulled backward to recover the hybrid braided stent.

Embodiment Two

As shown in FIG. 18, the stent body 20 in this embodiment is basically the same as the stent body 20 in the first embodiment one. For example, The stent body 20 in this embodiment, the same as the stent body 20 in the embodiment one, is also a tubular structure formed by interweaving at least two filaments, where the cross-sectional areas of at least two of the filaments are different, and the materials of the at least two filaments are different. The stent body 20 is formed by interweaving two or three kinds of filaments with different cross-sectional areas.

The difference between the stent body 20 in this embodiment and the stent body 20 in the embodiment one is that the stent body 20 in this embodiment includes at least two sections, and the weaving angles of the sections are not exactly the same, so as to better adapt to changes of the blood vessel.

For example, the stent body 20 in this embodiment includes two sections. In FIG. 18, the weaving angle a of the left section is larger, while the weaving angle a of the right section is smaller. The section with a larger weaving angle a is arranged at blood vessel with a larger diameter, while the section with a smaller weaving angle a is arranged at blood vessel with a smaller diameter. Each section can provide enough radial supporting force, and the section with a smaller weaving angle a has a smaller chronic outward force than the section with a larger weaving angle a, so that damage to blood vessels with a small diameter is reduced when the blood vessels are dilated.

In the case where the sections of the stent body 20 have the same diameter in this embodiment, different sections having different radial supporting forces and chronic outward forces have better applicability.

In the present application, the stent body is formed by interweaving at least two filaments, and at least two of the filaments have different end areas. The filament with a large end area provides the stent body with a sound supporting force so that the stent body fit closely with the blood vessel and good positioning is achieved. The filament with a small end area makes the mesh of the stent body small. When the stent body is mounted in the blood vessel, the plaque is stressed more uniformly and less likely to break. The stent body can effectively prevent the plaque fragments from flowing downstream in the blood vessel even if the plaque is broken.

In conclusion, the stent body of the application provides better safety during usage compared with the related art.

The invention claimed is:

1. A hybrid braided stent, comprising a stent body, wherein the stent body is a single-layer structure; the stent body is a tubular structure formed by interweaving a plurality of filaments, wherein cross-sectional areas of at least two of the plurality of the filaments are different;
   wherein the stent body is formed by braiding at least three kinds of filaments with different cross-sectional areas and different materials;
   wherein the stent body has a plurality of sections, weaving angles of at least two of the plurality of sections are different; and
   wherein the stent body comprises a section with a larger weaving angle and a section with a smaller weaving angle, the section with the larger weaving angle is sized and configured to be arranged in a blood vessel with a larger diameter, the section with the smaller weaving angle is sized and configured to be arranged in a blood vessel with a smaller diameter, and the section with the smaller weaving angle has a smaller outward force than the section with the larger weaving angle.

2. The hybrid braided stent according to claim 1, wherein the stent body is cylindrical or conical.

3. The hybrid braided stent according to claim 1, wherein at least one of the plurality of filaments is radiopaque.

4. They hybrid braided stent according to claim 1, wherein free ends of at least tow of the plurality of filaments located at an end of the stent body are connected together through a sleeve; or free ends of at least two of the plurality of filaments located at and end of the stent body are connected by welding to form a closed curve.

5. The hybrid braided stent according to claim 1, further comprising a dilator, wherein the dilator is mounted at an end of the stent body, and a diameter of the dilator is configured to gradually increase in a direction away from the stent body.

6. The hybrid braided stent according to claim 1, wherein a surface of each of the plurality of filaments is provided with a smooth insulating layer.

7. The hybrid braided stent according to claim 1, at least one of the plurality of filaments at an end of the stent body is provided with a bent portion, wherein the bent portion forms a socket configured to be inserted into by a protrusion of a delivery assembly.

* * * * *